United States Patent [19]

Singer

[11] Patent Number: 4,915,112

[45] Date of Patent: Apr. 10, 1990

[54] RADIOGRAPHIC MEASUREMENT DEVICE

[75] Inventor: Stuart J. Singer, Cambridge, Mass.

[73] Assignee: The Children's Medical Center Corporation, Boston, Mass.

[21] Appl. No.: 262,197

[22] Filed: Oct. 19, 1988

Related U.S. Application Data

[63] Continuation of Ser. No. 913,343, Sep. 30, 1986, abandoned.

[51] Int. Cl.⁴ .............................................. A61B 19/00
[52] U.S. Cl. ................................. 128/653 R; 33/512; 378/163
[58] Field of Search ............... 128/653, 654, 658, 659, 128/303 B, 781; 378/162–164, 204–207; 33/512

[56] References Cited

U.S. PATENT DOCUMENTS

| | | | |
|---|---|---|---|
| 2,293,324 | 8/1942 | Vladeff | 378/205 |
| 2,324,672 | 7/1943 | Bierman et al. | 128/781 |
| 3,547,121 | 12/1970 | Cherry | 378/164 |
| 3,812,842 | 5/1974 | Rodriguez | 378/163 |
| 3,941,127 | 3/1976 | Froning | 128/303 B |
| 4,048,507 | 9/1977 | de Gaston | 378/205 |
| 4,061,924 | 12/1977 | Jacoby et al. | 378/205 |
| 4,279,252 | 7/1981 | Martin | 128/658 |
| 4,583,538 | 4/1986 | Onik et al. | 128/653 |
| 4,692,936 | 9/1987 | Billeaudeaux | 378/163 |

FOREIGN PATENT DOCUMENTS 1088706  4/1985  U.S.S.R. .............. 128/653

Primary Examiner—Ruth S. Smith

[57] ABSTRACT

Measurement of a distance between two points within a body is aided by providing a planar scale that indicates at least one predetermined reference distance, and attaching the scale to the body in the same plane as the two points and in a location such that the scale will appear in a two-dimensional image taken of the body.

3 Claims, 2 Drawing Sheets

RADIOGRAPHIC MEASUREMENT DEVICE

This is a continuation of co-pending application Ser. No. 913,340 filed on Sept. 30, 1986, now abandoned.

BACKGROUND OF THE INVENTION

This invention relates to measuring the distance between two points within a body.

With respect to a human body, measurement errors as small as 1 mm can be significant. For example, a distance of 3.5 mm between the atlas and axis spinal bones may be normal while a distance of 4.5 mm may indicate atlanto-axial subluxation requiring further evaluation. And small changes in the distance over time may be important to diagnosis.

It is known to use a conventional ruler to measure distances directly on the X-ray film. Sometimes special rulers (having radio opaque material embedded in the index lines along the ruler) are placed at a location either between the X-ray source and the body, or between the body and the X-ray film. The X-ray film will then bear an image of the ruler's index lines that aid in measuring distances on the film.

Pelvimetry measuring devices have stable bases that rests on the same surface as the person's body. A ruler is attached to the base in a way that permits it to be adjusted in height and orientation to lie on top of the abdomen.

In typical X-ray techniques, distances on the image of the X-ray film are either enlarged or reduced relative to real distances in the body.

Some radio opaque rulers include a wooden base that slightly raises the scale purportedly to be in a similar plane with, for example, the bones of the leg.

SUMMARY OF THE INVENTION

A general feature of the invention is in aiding measurement of a distance between two points within a body by providing a planar scale that indicates at least one predetermined reference distance, and attaching the scale to the body in the same plane as the two points and in a location such that the scale will appear in a two-dimensional image taken of the body.

Preferred embodiments include the following features. The scale is attached to the body using a rigid member having a surface perpendicular to the plane of interest and adapted to rest on an external surface of the body. An extended flexible member (e.g., a velcro strap) surrounds the body to keep the scale attached. The scale has more opaque portions and less opaque portions, and includes a planar jacket having uniform opacity that is selected based on the sensitivity of the image medium. When the angle between the plane of the scale and the plane of the image is greater than a predetermined amount, a less radio opaque aperture in an opaque region of the scale ceases to pass the imaging beam, giving a direct visual indication on the image. The scale comprises a series of more opaque regions and less opaque regions all of the same width.

Accurate, repeatable distance measurements are made possible. Any enlargement or reduction of distances in the image relative to the body that result from the imaging technique will similarly affect the size of the scale in the image. The scale thus enables accurate measurement. Attaching the scale to the body assures that any movement of the body prior to exposing the image will not shift the scale out of the desired plane.

Other advantages and features will become apparent from the following description of the preferred embodiment and from the claims.

DESCRIPTION OF THE PREFERRED EMBODIMENT

We first briefly describe the drawings.

STRUCTURE

Figure 1:
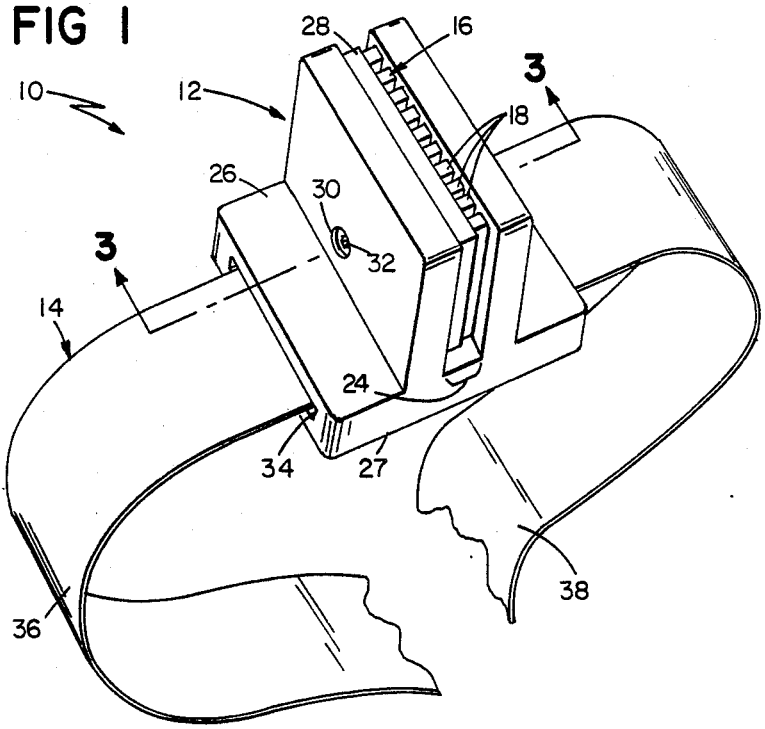
FIG. 1 is a perspective view of a radiographic measurement device.

Referring to FIG. 1, a radiographic measuring device 10 includes an assembly 12 and a strap 14 for holding assembly 12 in position on a person's body. Assembly 12 includes a radio opaque scale in the form of a comb 16.

Figure 2:
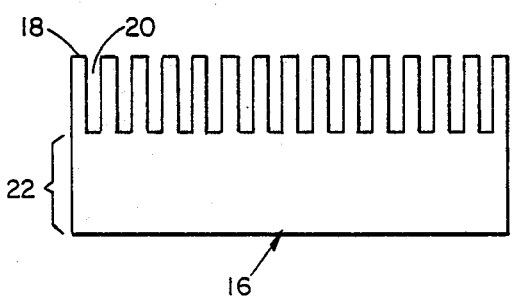
FIG. 2 is a front view of a comb of the device of FIG. 1.

Referring to FIG. 2, comb 16 is a 1/16 inch thick copper plate bearing a series of 1 mm wide tines 18 separated by 1 mm wide gaps 20. Tines 18 are each 5 mm long, and are supported on a base 22 that is 7 mm high and 30 mm long.

Figure 3:
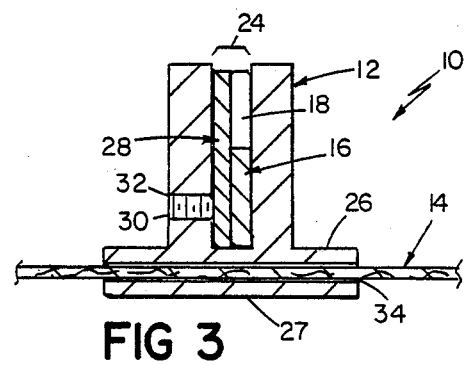
FIG. 3 is a cross-sectional view at 3—3 of FIG. 1.
Figure 4:
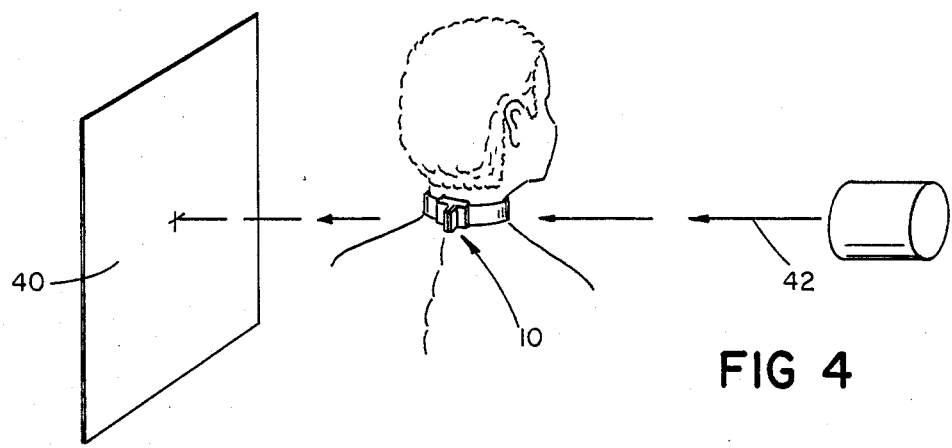
FIG. 4 is a diagram showing the device in use.

Referring again to FIG. 1, and also to FIG. 3, comb 16 lies within a ¼" thick slot 24 in an acrylic support 26 together with a 1/16" thick plain rectangular copper jacket 28. Comb 16 and jacket 28 are secured by a copper set screw 30 lying within a threaded hole in support 26. Set screw 30 is 4 mm in diameter and has a central recess 32 2 mm wide and about 2 mm deep and configured to receive a hex wrench. Support 26 has a channel 34, in which strap 14 is held and a bottom surface 27 that lies against the patient's skin, and is perpendicular to the comb. Strap 14 has hook-type velcro material on the outside layer 36 and pile-type velcro material on the inside layer 38 for securing the strap.

USE

To use device 10 to aid in radiographic measurement of, for example, the atlanto-axial distance when the spine is in flexion, device 10 is strapped around the patient's neck and adjusted so that comb 12 lies on the midline overlying the spinal processes, that is, in the same plane as the atlas and axis bones. The patient is positioned near X-ray film 40, so that comb 16 and the plane of the bones are parallel to the plane of film 40 and perpendicular to the X-ray beam 42. The film is then exposed in a conventional manner.

Figure 5:
FIG. 5 is a lateral X-ray of a spine in extension.

Referring to FIG. 5 (showing an X-ray of a spine in extension when the comb 16 was held on the front of the patient's neck, over the thyroid cartilage), tines 18 and gaps 20 are clearly visible. By adjusting a caliper to the atlanto-axial distance to be measured and then laying the caliper over the scale represented by the tines and gaps, the atlanto-axial distance is accurately measured. Because the comb 16 was held in the same plane as the bones, any enlargement or reduction in the image of the bones caused by the X-ray technique being used (which can be as much as 40%) has an identical effect on the image of the tines and gaps. Thus, the image of each tine and each gap accurately represents a distance of 1 mm in the image of the patient's spine. The number of tines and gaps encompassed by the caliper represents the number of millimeters separating the atlas and axis bones.

In FIG. 5, the black arrow on the comb points to the image of set screw 30. Because recess 32 is not as radio opaque as the surrounding portion of screw 30, the center portion of the image of set screw 30 appears somewhat darker. If that center portion were not darker, it would indicate that the comb had been in a plane at an angle greater than some predetermined amount, for example greater than 30°, to the plane of the film (obscuring the free passage of the beam through recess 32). In that case, the X-ray should be taken again because the image of comb 16 would not provide a sufficiently accurate measurement scale.

The device can also be used to aid measurement of other structures, for example, the thickness of prevertebral soft tissue, the alignment of vertebral bodies, the degree of deviation of the C-2 spinolaminar line from the posterior cervical line, and vessel diameters in angiographic images.

Because the device can be easily and repeatedly positioned with comb 16 in the plane of the structure being measured, changes in distances over time can be accurately determined by taking successive X-ray images, even when different radiographic techniques or patient positions are used.

The jacket 24 filters the X-ray beam so that the relative exposure levels of the tines and gaps fall within the linear portion of the sensitivity of the film.

Because the comb comprises equal sized tines and gaps, measurements can be more accurately made than if a traditional ruler having spaced apart thin index lines were used.

Other embodiments are within the following claims. For example, recess 32 could be deliberately drilled as a predetermined diameter hole in a conventional slotted screw.

I claim:

1. A device for aiding accurate measurement of the distance between two points within the body of a patient in conjunction with an imaging technique which produces a two-dimensional image that includes a representation of said distance, said two-dimensional image being produced by a beam passing through said body in a predetermined direction, said two points lying in a plane generally perpendicular to said predetermined beam direction, said device comprising:

a planar scale having a series of opaque regions along the length of said scale, a boundary between each opaque region and the next opaque region being perpendicular to said length of said scale, and wherein there is a difference in opacity between each opaque region and the next adjacent opaque region, whereby distances along the length of said scale are accurately represented with reference to said boundaries, and a support attached to said scale and adapted for affixing said scale on the outside of said body, said support including a rigid member having a contact surface that is perpendicular to said plane of said opaque regions and adapted to rest against an external surface of said body so that, notwithstanding motion of said body, said opaque regions on said planar scale are held in the same plane as said two points and in a location such that said scale will be represented in said image, and a means for imparting in said image a visual indication of whether or not the orientation of the plane of said scale relative to the plane of said two-dimensional image is greater than a predetermined amount.

2. The device of claim 1 wherein said support further includes means for attaching said scale to said body, said attaching means comprising an extended flexible member adapted to surround said body.

3. The device of claim 1 wherein said imaging technique comprises a beam passing through said scale and different said opaque regions cause different degrees of attenuation of said beam, and said scale further comprises a planar jacket that overlies said opaque regions and causes a uniform degree of attenuation of said beam, said uniform degree being selected based on the sensitivity of a medium on which said two-dimensional image is formed.

* * * * *